US008317855B2

(12) United States Patent
Gregorich et al.

(10) Patent No.: US 8,317,855 B2
(45) Date of Patent: Nov. 27, 2012

(54) CRIMPABLE AND EXPANDABLE SIDE BRANCH CELL

(75) Inventors: Daniel Gregorich, St. Louis Park, MN (US); Michael P. Meyer, Richfield, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1523 days.

(21) Appl. No.: 11/138,022

(22) Filed: May 26, 2005

(65) Prior Publication Data
US 2006/0271159 A1    Nov. 30, 2006

(51) Int. Cl.
A61F 2/06    (2006.01)
(52) U.S. Cl. ...................................... 623/1.35
(58) Field of Classification Search ................ 623/1.16, 623/1.35
See application file for complete search history.

(56) References Cited

U.S. PATENT DOCUMENTS

| | | | |
|---|---|---|---|
| 4,309,994 A | 1/1982 | Grunwald | 128/214 R |
| 4,769,005 A | 9/1988 | Ginsburg et al. | 604/53 |
| 4,774,949 A | 10/1988 | Fogarty | 128/348.1 |
| 4,896,670 A | 1/1990 | Crittenden | 606/194 |
| 4,905,667 A | 3/1990 | Foerster et al. | 128/4 |
| 4,994,071 A | 2/1991 | MacGregor | 606/194 |
| 5,342,387 A | 8/1994 | Summers | 606/198 |
| 5,387,235 A | 2/1995 | Chuter | 623/1 |
| 5,456,712 A | 10/1995 | Maginot | 623/1 |
| 5,476,471 A | 12/1995 | Shifrin et al. | 606/151 |
| 5,487,730 A | 1/1996 | Marcadis et al. | 604/96 |
| 5,591,228 A | 1/1997 | Edoga | 623/1 |
| 5,596,020 A | 1/1997 | Morris | 516/646 |
| 5,607,444 A | 3/1997 | Lam | 606/194 |
| 5,609,605 A | 3/1997 | Marshall et al. | 606/191 |
| 5,609,627 A | 3/1997 | Goicoechea et al. | 623/1 |
| 5,613,980 A | 3/1997 | Chauhan | 606/194 |
| 5,617,878 A | 4/1997 | Taheri | 128/898 |
| 5,632,762 A | 5/1997 | Myler | 606/194 |
| 5,632,763 A | 5/1997 | Glastra | 606/194 |
| 5,632,772 A | 5/1997 | Alcime et al. | 623/1 |
| 5,636,641 A | 6/1997 | Fariabi | 600/585 |
| 5,669,924 A | 9/1997 | Shaknovich | 606/108 |
| 5,669,932 A | 9/1997 | Fischell et al. | 606/198 |

(Continued)

FOREIGN PATENT DOCUMENTS

CA    2220864    7/1999

(Continued)

OTHER PUBLICATIONS

U.S. Appl. No. 09/325,996, filed Jun. 4, 1999, Vardi et al.

(Continued)

Primary Examiner — Brian Pellegrino
(74) Attorney, Agent, or Firm — Vidas, Arrett & Steinkraus

(57) ABSTRACT

A stent may include a side branch cell comprising a plurality of petals. Each petal may comprise struts and turns, and may have a longitudinal axis oriented at an angle to the stent longitudinal axis. Each petal may include a plurality of straight struts which are substantially parallel to the stent longitudinal axis. Each petal may include at least one appendage which may be oriented substantially parallel to the stent longitudinal axis, and which may remain substantially parallel to the stent longitudinal axis as the stent is deployed. The dimension of the side branch cell about the circumference of the stent may increase more than the dimension of the side branch cell in a stent lengthwise directions as the stent is expanded.

23 Claims, 4 Drawing Sheets

U.S. PATENT DOCUMENTS

| | | | |
|---|---|---|---|
| 5,676,697 A | 10/1997 | McDonald | 623/1 |
| 5,683,450 A | 11/1997 | Goicoechea et al. | 623/1 |
| 5,697,971 A | 12/1997 | Fischell et al. | 623/1 |
| 5,707,348 A | 1/1998 | Krogh | 602/41 |
| 5,709,713 A | 1/1998 | Evans et al. | 623/1 |
| 5,720,735 A | 2/1998 | Dorros | 604/284 |
| 5,749,825 A | 5/1998 | Fischell et al. | 600/3 |
| 5,749,890 A | 5/1998 | Shaknovich | 606/198 |
| 5,755,734 A | 5/1998 | Richter et al. | 606/194 |
| 5,755,735 A | 5/1998 | Richter et al. | 606/194 |
| 5,755,771 A | 5/1998 | Penn et al. | 623/1 |
| 5,755,773 A | 5/1998 | Evans et al. | 623/1 |
| 5,755,778 A | 5/1998 | Kleshinski | 623/1 |
| 5,782,906 A | 7/1998 | Marshall et al. | 623/1 |
| 5,824,036 A | 10/1998 | Lauterjung | 623/1 |
| 5,824,040 A | 10/1998 | Cox et al. | 623/1 |
| 5,827,320 A | 10/1998 | Richter et al. | 606/194 |
| 5,851,464 A | 12/1998 | Davila et al. | 264/103 |
| 5,868,777 A | 2/1999 | Lam | 606/194 |
| 5,893,887 A | 4/1999 | Jayaraman | 623/1 |
| 5,922,021 A | 7/1999 | Jang | 623/1 |
| 5,961,548 A | 10/1999 | Shmulewitz | 623/1 |
| 5,972,017 A | 10/1999 | Berg et al. | 606/198 |
| 6,013,054 A | 1/2000 | Jiun Yan | 604/96 |
| 6,013,091 A | 1/2000 | Ley et al. | 606/191 |
| 6,017,324 A | 1/2000 | Tu et al. | 604/96 |
| 6,017,363 A | 1/2000 | Hojeibane | 623/1 |
| 6,030,414 A | 2/2000 | Taheri | 623/1 |
| 6,033,434 A | 3/2000 | Borghi | 623/1 |
| 6,033,435 A | 3/2000 | Penn et al. | 623/1 |
| 6,056,775 A | 5/2000 | Borghi et al. | 623/1.16 |
| 6,059,824 A | 5/2000 | Taheri | 623/1 |
| 6,068,655 A | 5/2000 | Seguin et al. | 623/1 |
| 6,086,611 A | 7/2000 | Duffy et al. | 623/1 |
| 6,093,203 A | 7/2000 | Uflacker | 612/1.12 |
| 6,096,073 A | 8/2000 | Webster et al. | 623/1.16 |
| 6,099,497 A | 8/2000 | Adams et al. | 604/96.01 |
| 6,113,579 A | 9/2000 | Eidenschink et al. | 604/264 |
| 6,117,117 A | 9/2000 | Mauch | 604/284 |
| 6,117,156 A | 9/2000 | Richter et al. | 606/194 |
| 6,123,721 A | 9/2000 | Jang | 623/1.6 |
| 6,129,738 A | 10/2000 | Lashinski et al. | 606/194 |
| 6,142,973 A | 11/2000 | Carleton et al. | 604/96 |
| 6,143,002 A | 11/2000 | Vietmeier | 606/108 |
| 6,159,238 A | 12/2000 | Killion et al. | 612/1.11 |
| 6,165,195 A | 12/2000 | Wilson et al. | 606/194 |
| 6,168,621 B1 | 1/2001 | Vrba | 623/1.2 |
| 6,183,509 B1 | 2/2001 | Dibie | 623/1.35 |
| 6,203,568 B1 | 3/2001 | Lombardi et al. | 623/1.13 |
| 6,210,380 B1 | 4/2001 | Mauch | 604/284 |
| 6,210,429 B1 | 4/2001 | Vardi et al. | 623/1.11 |
| 6,210,433 B1 | 4/2001 | Larre | 623/1.15 |
| 6,231,599 B1 * | 5/2001 | Ley | 623/1.15 |
| 6,254,593 B1 | 7/2001 | Wilson | 606/1.11 |
| 6,258,115 B1 | 7/2001 | Dubrul | 606/200 |
| 6,258,116 B1 | 7/2001 | Hojeibane | 623/1.16 |
| 6,261,305 B1 | 7/2001 | Marotta et al. | 606/200 |
| 6,261,316 B1 | 7/2001 | Shaolian et al. | 623/1.11 |
| 6,264,662 B1 | 7/2001 | Lauterjung | 606/108 |
| 6,264,686 B1 | 7/2001 | Rieu et al. | 623/1.16 |
| 6,290,673 B1 | 9/2001 | Shanley | 604/102.02 |
| 6,293,968 B1 | 9/2001 | Taheri | 623/1.15 |
| 6,325,826 B1 * | 12/2001 | Vardi et al. | 623/1.35 |
| 6,334,864 B1 | 1/2002 | Amplatz et al. | 606/200 |
| 6,334,870 B1 | 1/2002 | Ehr | 623/1.5 |
| 6,346,089 B1 | 2/2002 | Dibie | 603/1.15 |
| 6,348,065 B1 | 2/2002 | Brown | 623/1 |
| 6,355,060 B1 | 3/2002 | Lenker et al. | 623/1.34 |
| 6,361,544 B1 | 3/2002 | Wilson et al. | 606/194 |
| 6,361,555 B1 | 3/2002 | Wilson | 623/1.11 |
| 6,383,213 B2 | 5/2002 | Wilson et al. | 623/1.11 |
| 6,395,018 B1 | 5/2002 | Castaneda | 623/1.13 |
| 6,436,104 B2 | 8/2002 | Hojeibane | 606/108 |
| 6,436,134 B2 | 8/2002 | Richter et al. | 623/1.15 |
| 6,478,816 B1 | 11/2002 | Kveen et al. | 633/1.15 |
| 6,508,836 B2 | 1/2003 | Wilson et al. | 623/1.35 |
| 6,517,558 B2 | 2/2003 | Gittings et al. | 606/153 |
| 6,520,988 B1 | 2/2003 | Colombo et al. | 623/1.35 |
| 6,540,779 B2 | 4/2003 | Richter et al. | 623/1.35 |
| 6,579,309 B1 | 6/2003 | Loos et al. | 623/1.16 |
| 6,579,312 B2 | 6/2003 | Wilson et al. | 623/1.35 |
| 6,582,394 B1 | 6/2003 | Reiss et al. | 604/96.01 |
| 6,596,020 B2 | 7/2003 | Vardi et al. | 623/1.11 |
| 6,599,316 B2 | 7/2003 | Vardi et al. | 623/1.15 |
| 6,645,242 B1 | 11/2003 | Quinn | 623/1.16 |
| 6,689,156 B1 | 2/2004 | Davidson et al. | 623/1.11 |
| 6,692,483 B2 | 2/2004 | Vardi et al. | 604/529 |
| 6,695,877 B2 | 2/2004 | Brucker et al. | 623/1.16 |
| 6,706,062 B2 | 3/2004 | Vardi et al. | 623/1.15 |
| 6,749,628 B1 | 6/2004 | Callol et al. | 623/1.15 |
| 6,776,793 B2 | 8/2004 | Brown et al. | 623/1.15 |
| 6,811,566 B1 | 11/2004 | Penn et al. | 623/1.15 |
| 6,835,203 B1 | 12/2004 | Vardi et al. | 623/1.34 |
| 6,858,038 B2 | 2/2005 | Heuser | 623/1.35 |
| 6,884,258 B2 | 4/2005 | Vardi et al. | 623/1.11 |
| 6,896,699 B2 | 5/2005 | Wilson et al. | 623/1.35 |
| 6,932,837 B2 | 8/2005 | Amplatz et al. | 623/1.15 |
| 6,955,687 B2 | 10/2005 | Richter et al. | 623/1.35 |
| 6,955,688 B2 | 10/2005 | Wilson et al. | 623/1.35 |
| 6,962,602 B2 | 11/2005 | Vardi et al. | 623/1.11 |
| 7,018,400 B2 | 3/2006 | Lashinski et al. | 623/1.11 |
| 7,056,323 B2 | 6/2006 | Mareiro et al. | 606/108 |
| 7,060,091 B2 | 6/2006 | Killion et al. | 623/1.15 |
| 7,220,275 B2 * | 5/2007 | Davidson et al. | 623/1.35 |
| 2001/0003161 A1 | 6/2001 | Vardi et al. | 623/1.11 |
| 2001/0004706 A1 | 6/2001 | Hojeibane | 623/1.11 |
| 2001/0004707 A1 | 6/2001 | Dereurne et al. | 623/1.16 |
| 2001/0012927 A1 | 8/2001 | Mauch | 604/284 |
| 2001/0016766 A1 | 8/2001 | Vardi et al. | 623/1.11 |
| 2001/0016767 A1 | 8/2001 | Wilson et al. | 623/1.11 |
| 2001/0016768 A1 | 8/2001 | Wilson et al. | 623/1.11 |
| 2001/0025195 A1 | 9/2001 | Shaolian et al. | 623/1.13 |
| 2001/0027291 A1 | 10/2001 | Shanley | 604/104 |
| 2001/0027338 A1 | 10/2001 | Greenberg | 623/1.13 |
| 2001/0029396 A1 | 10/2001 | Wilson et al. | 623/1.11 |
| 2001/0037116 A1 | 11/2001 | Wilson et al. | 606/108 |
| 2001/0037138 A1 | 11/2001 | Wilson et al. | 623/1.11 |
| 2001/0039448 A1 | 11/2001 | Dibie | 623/1.16 |
| 2001/0049552 A1 | 12/2001 | Richter et al. | 623/1.15 |
| 2001/0056297 A1 | 12/2001 | Hojeibane | 623/1.16 |
| 2002/0013618 A1 | 1/2002 | Marotta et al. | 623/1.15 |
| 2002/0013619 A1 | 1/2002 | Shanley | 623/1.15 |
| 2002/0022874 A1 | 2/2002 | Wilson | 623/1.11 |
| 2002/0026232 A1 | 2/2002 | Marotta et al. | 623/1.16 |
| 2002/0035392 A1 | 3/2002 | Wilson | 623/1.11 |
| 2002/0042650 A1 | 4/2002 | Vardi et al. | 623/1.35 |
| 2002/0052648 A1 | 5/2002 | McGuckin, Jr. et al. | 623/1.35 |
| 2002/0072790 A1 | 6/2002 | McGuckin, Jr. et al. | 623/1.12 |
| 2002/0111675 A1 | 8/2002 | Wilson | 623/1.35 |
| 2002/0156516 A1 | 10/2002 | Vardi et al. | 623/1.11 |
| 2002/0156517 A1 | 10/2002 | Perouse | 623/1.11 |
| 2002/0165604 A1 | 11/2002 | Shanley | 623/1.15 |
| 2002/0173835 A1 | 11/2002 | Bourang et al. | 623/1.11 |
| 2002/0173840 A1 | 11/2002 | Brucker et al. | 623/1.16 |
| 2002/0183763 A1 | 12/2002 | Callol et al. | 606/108 |
| 2002/0193872 A1 | 12/2002 | Trout, III et al. | 623/1.34 |
| 2002/0193873 A1 | 12/2002 | Brucker et al. | 623/1.35 |
| 2003/0009209 A1 | 1/2003 | Hojeibane | 623/1.11 |
| 2003/0028233 A1 | 2/2003 | Vardi et al. | 623/1.11 |
| 2003/0050688 A1 | 3/2003 | Fischell et al. | 623/1.15 |
| 2003/0055378 A1 | 3/2003 | Wang et al. | 604/103.07 |
| 2003/0055483 A1 | 3/2003 | Gumm | 623/1.11 |
| 2003/0074047 A1 | 4/2003 | Richter | 623/1.11 |
| 2003/0093109 A1 | 5/2003 | Mauch | 606/194 |
| 2003/0097169 A1 | 5/2003 | Brucker | 623/1.11 |
| 2003/0114912 A1 | 6/2003 | Sequin et al. | 623/1.11 |
| 2003/0125791 A1 | 7/2003 | Sequin et al. | 623/1.11 |
| 2003/0125802 A1 | 7/2003 | Callol et al. | 623/1.35 |
| 2003/0135259 A1 | 7/2003 | Simso | 623/1.12 |
| 2003/0181923 A1 | 9/2003 | Vardi | 606/108 |
| 2003/0195606 A1 | 10/2003 | Davidson et al. | 623/1.11 |
| 2004/0006381 A1 | 1/2004 | Sequin et al. | 623/1.12 |
| 2004/0015227 A1 | 1/2004 | Vardi et al. | 623/1.16 |
| 2004/0044396 A1 | 3/2004 | Clerc et al. | 623/1.13 |
| 2004/0059406 A1 | 3/2004 | Cully et al. | 623/1.11 |
| 2004/0088007 A1 | 5/2004 | Eidenschink | 607/1 |
| 2004/0117003 A1 | 6/2004 | Ouriel et al. | 623/1.35 |

| | | | |
|---|---|---|---|
| 2004/0133268 A1 | 7/2004 | Davidson et al. | 623/1.35 |
| 2004/0138732 A1 | 7/2004 | Suhr et al. | 623/1.11 |
| 2004/0138737 A1 | 7/2004 | Davidson et al. | 623/1.35 |
| 2004/0148006 A1 | 7/2004 | Davidson et al. | 623/1.11 |
| 2004/0172121 A1 | 9/2004 | Eidenschink et al. | 623/1.11 |
| 2004/0186560 A1 | 9/2004 | Alt | 623/1.35 |
| 2004/0225345 A1 | 11/2004 | Fischell et al. | 623/1.11 |
| 2004/0267352 A1* | 12/2004 | Davidson et al. | 623/1.15 |
| 2005/0004656 A1 | 1/2005 | Das | 623/1.16 |
| 2005/0010278 A1 | 1/2005 | Vardi et al. | 623/1.15 |
| 2005/0015108 A1 | 1/2005 | Williams et al. | 606/194 |
| 2005/0015135 A1 | 1/2005 | Shanley | 623/1.11 |
| 2005/0060027 A1 | 3/2005 | Khenansho et al. | 623/1.35 |
| 2005/0096726 A1 | 5/2005 | Sequin et al. | 623/1.12 |
| 2005/0102021 A1 | 5/2005 | Osborne | 623/1.13 |
| 2005/0102023 A1 | 5/2005 | Yadin et al. | 623/1.15 |
| 2005/0119731 A1 | 6/2005 | Brucker et al. | 623/1.35 |
| 2005/0125076 A1 | 6/2005 | Ginn | 623/23.65 |
| 2005/0131526 A1 | 6/2005 | Wong | 623/1.15 |
| 2005/0149161 A1 | 7/2005 | Eidenschink et al. | 623/1.11 |
| 2005/0154442 A1 | 7/2005 | Eidenschink et al. | 623/1.11 |
| 2005/0154444 A1 | 7/2005 | Quadri | 623/1.13 |
| 2005/0183259 A1 | 8/2005 | Eidenschink et al. | 29/508 |
| 2005/0209673 A1 | 9/2005 | Shaked | 623/1.11 |
| 2005/0228483 A1 | 10/2005 | Kaplan et al. | 623/1.15 |
| 2006/0036315 A1 | 2/2006 | Yadin et al. | 623/1.35 |
| 2006/0041303 A1 | 2/2006 | Israel | 623/1.11 |
| 2006/0079956 A1 | 4/2006 | Eigler et al. | 623/1.35 |
| 2006/0173528 A1 | 8/2006 | Feld et al. | 623/1.15 |
| 2007/0073376 A1 | 3/2007 | Krolik et al. | 623/1.11 |

FOREIGN PATENT DOCUMENTS

| | | |
|---|---|---|
| DE | 9014845 | 2/1991 |
| DE | 29701758 | 3/1997 |
| DE | 29701883 | 5/1997 |
| EP | 0479730 | 10/1991 |
| EP | 0751752 | 1/1997 |
| EP | 0783873 | 7/1997 |
| EP | 0804907 | 11/1997 |
| EP | 0479557 | 7/1998 |
| EP | 0876805 | 11/1998 |
| EP | 0880949 | 12/1998 |
| EP | 0891751 | 1/1999 |
| EP | 0895759 | 2/1999 |
| EP | 0904745 | 3/1999 |
| EP | 0937442 | 8/1999 |
| EP | 0347023 | 12/1999 |
| EP | 1031328 | 8/2000 |
| EP | 1031329 | 8/2000 |
| EP | 0883384 | 12/2000 |
| EP | 0862392 | 8/2001 |
| EP | 0808140 | 12/2001 |
| EP | 0884028 | 2/2002 |
| EP | 1190685 | 3/2002 |
| EP | 0897700 | 7/2002 |
| EP | 0684022 | 2/2004 |
| EP | 1157674 | 7/2005 |
| EP | 1031330 | 11/2005 |
| EP | 1070513 | 6/2006 |
| FR | 2678508 | 1/1993 |
| FR | 2740346 | 10/1995 |
| FR | 2756173 | 11/1996 |
| GB | 2337002 | 5/1998 |
| WO | 88/06026 | 8/1988 |
| WO | 95/21592 | 8/1995 |
| WO | 96/29955 | 10/1996 |
| WO | 96/34580 | 11/1996 |
| WO | 96/41592 | 12/1996 |
| WO | 97/07752 | 3/1997 |
| WO | 97/15346 | 5/1997 |
| WO | 97/16217 | 5/1997 |
| WO | 97/26936 | 7/1997 |
| WO | 97/41803 | 11/1997 |
| WO | 97/45073 | 12/1997 |
| WO | 97/46174 | 12/1997 |
| WO | 98/19628 | 5/1998 |
| WO | 98/36709 | 8/1998 |
| WO | 98/37833 | 9/1998 |
| WO | 98/47447 | 10/1998 |
| WO | 98/48879 | 11/1998 |
| WO | 99/03426 | 1/1999 |
| WO | 99/04726 | 2/1999 |
| WO | 99/15103 | 4/1999 |
| WO | 99/15109 | 4/1999 |
| WO | 99/24104 | 5/1999 |
| WO | 99/34749 | 7/1999 |
| WO | 99/36002 | 7/1999 |
| WO | 99/36015 | 7/1999 |
| WO | 99/44539 | 9/1999 |
| WO | 99/56661 | 11/1999 |
| WO | 99/65419 | 12/1999 |
| WO | 00/07523 | 2/2000 |
| WO | 00/10489 | 3/2000 |
| WO | 00/16719 | 3/2000 |
| WO | 00/27307 | 5/2000 |
| WO | 00/27463 | 5/2000 |
| WO | 00/28922 | 5/2000 |
| WO | 01/45594 | 6/2000 |
| WO | 00/44307 | 8/2000 |
| WO | 00/44309 | 8/2000 |
| WO | 00/47134 | 8/2000 |
| WO | 00/48531 | 8/2000 |
| WO | 00/49951 | 8/2000 |
| WO | 00/51523 | 9/2000 |
| WO | 00/57813 | 10/2000 |
| WO | 00/67673 | 11/2000 |
| WO | 00/71054 | 11/2000 |
| WO | 00/71055 | 11/2000 |
| WO | 00/74595 | 12/2000 |
| WO | 01/21095 | 3/2001 |
| WO | 01/21109 | 3/2001 |
| WO | 01/21244 | 3/2001 |
| WO | 01/35715 | 5/2001 |
| WO | 01/35863 | 5/2001 |
| WO | 01/39697 | 6/2001 |
| WO | 01/39699 | 6/2001 |
| WO | 01/41677 | 6/2001 |
| WO | 01/43665 | 6/2001 |
| WO | 01/43809 | 6/2001 |
| WO | 01/45785 | 6/2001 |
| WO | 01/49342 | 7/2001 |
| WO | 01/54621 | 8/2001 |
| WO | 01/54622 | 8/2001 |
| WO | 01/58385 | 8/2001 |
| WO | 01/60284 | 8/2001 |
| WO | 01/70294 | 9/2001 |
| WO | 01/70299 | 9/2001 |
| WO | 01/74273 | 10/2001 |
| WO | 01/89409 | 11/2001 |
| WO | 02/00138 | 1/2002 |
| WO | 02/053066 | 7/2002 |
| WO | 02/068012 | 9/2002 |
| WO | 03/007842 | 1/2003 |
| WO | 03/055414 | 7/2003 |
| WO | 03/063924 | 8/2003 |
| WO | 2004/026174 | 4/2004 |
| WO | 2004/026180 | 4/2004 |
| WO | 2005/009295 | 2/2005 |
| WO | 2005/014077 | 2/2005 |
| WO | 2006/028925 | 3/2006 |

OTHER PUBLICATIONS

U.S. Appl. No. 09/614,472, filed Jul. 11, 2000 Davidson et al.
U.S. Appl. No. 09/663,111, filed Sep. 15, 2000, Davidson et al.
Chevalier, M.D., Bernard, "Placement of Coronary Stents in Bifurcation Lesions by the "Culotte" Technique," *The American Journal of Cardiology*, vol. 82, pp. 943-949 (Oct. 15, 1998).
Nakamura M.D., Shigeru, "Techniques for Palmaz-Schatz Stent Deployment in Lesions with a Large Side Branch," *Catheterization and Cardiovascular Diagnosis*, vol. 34, pp. 353-361 (1995).
Caputo, Ronald P., "Stent Jail: A Minimum-Security Prison," *The American Journal of Cardiology*, vol. 77, pp. 1226-1230 (Jun. 1, 1996).
Colombo, M.D., Antonio, "Kissing" Stent for Bifurcational Coronary Lesion, *Catheterization and Cardiovascular Diagnosis*, vol. 30, pp. 327-330 (Dec. 1993).

Carrie, M.D., Didier, "T"-Shaped Stent Placement: A Technique for the Treatment of Dissected Bifurcation Lesions, *Catheterization and Cardiovascular Diagnosis*, vol. 37, pp. 311-313 (Mar. 1996).

Katoh, M.D., Osamu, "New Double Wire Technique to Stent Ostial Lesions," *Catheterization and Cardiovascular Diagnosis*, vol. 40, pp. 400-402 (Apr. 1997).

Lewis, M.D., Bruce E., "Acute procedural results in the treatment of 30 coronary artery bifurcation lesions with a double-wire atherectomy technique for side-branch protection," *American Heart Journal*, vol. 127:6, pp. 1600-1607 (Jun. 1994).

Yamashita, M.D.,PhD., Takehiro, "Bifurcation Lesions: Two Stents Versus One Stent—Immediate and Follow-up Results," *Journal of the American College of Cardiology*, vol. 35:5, pp. 1145-1151 (Apr. 2000).

Satler, M.D., Lowell F., "Bifurcation Disease: To Treat or Not to Treat," *Catheterization and Cardiovascular Interventions*, vol. 50, pp. 411-412 (2000).

* cited by examiner

CRIMPABLE AND EXPANDABLE SIDE BRANCH CELL

BACKGROUND OF THE INVENTION

1. Field of the Invention

In some embodiments this invention relates to implantable medical devices, their manufacture, and methods of use. Some embodiments are directed to delivery systems, such as catheter systems of all types, which are utilized in the delivery of such devices.

2. Description of the Related Art

A stent is a medical device introduced to a body lumen and is well known in the art. Typically, a stent is implanted in a blood vessel at the site of a stenosis or aneurysm endoluminally, i.e. by so-called "minimally invasive techniques" in which the stent in a radially reduced configuration, optionally restrained in a radially compressed configuration by a sheath and/or catheter, is delivered by a stent delivery system or "introducer" to the site where it is required. The introducer may enter the body from an access location outside the body, such as through the patient's skin, or by a "cut down" technique in which the entry blood vessel is exposed by minor surgical means.

Stents, grafts, stent-grafts, vena cava filters, expandable frameworks, and similar implantable medical devices, collectively referred to hereinafter as stents, are radially expandable endoprostheses which are typically intravascular implants capable of being implanted transluminally and enlarged radially after being introduced percutaneously. Stents may be implanted in a variety of body lumens or vessels such as within the vascular system, urinary tracts, bile ducts, fallopian tubes, coronary vessels, secondary vessels, etc. Stents may be used to reinforce body vessels and to prevent restenosis following angioplasty in the vascular system. They may be self-expanding, expanded by an internal radial force, such as when mounted on a balloon, or a combination of self-expanding and balloon expandable (hybrid expandable).

Stents may be created by methods including cutting or etching a design from a tubular stock, from a flat sheet which is cut or etched and which is subsequently rolled or from one or more interwoven wires or braids.

Within the vasculature, it is not uncommon for stenoses to form at a vessel bifurcation. A bifurcation is an area of the vasculature or other portion of the body where a first (or parent) vessel is bifurcated into two or more branch vessels. Where a stenotic lesion or lesions form at such a bifurcation, the lesion(s) can affect only one of the vessels (i.e., either of the branch vessels or the parent vessel) two of the vessels, or all three vessels. Many prior art stents however are not wholly satisfactory for use where the site of desired application of the stent is juxtaposed or extends across a bifurcation in an artery or vein such, for example, as the bifurcation in the mammalian aortic artery into the common iliac arteries.

Stents for use in bifurcated regions are generally known. When treating a bifurcated vessel, it may desirable to use a stent having a side branch opening configured to provide fluid communication between the primary vessel and a secondary or branch vessel of the bifurcation. A secondary or branch stent may be received within and/or be positioned adjacent to the side branch opening of the primary stent.

A side opening in some stents may further include a structural component, which when deployed, extends from the primary stent and into the branch vessel. In some instances a side branch structure (e.g. limb, arm, branch, etc.) exhibits expansion characteristics that are different from other portions of the primary stent. In some instances, it may be difficult to initiate an outward expansion of the side branch. In some instances, strut members of the stent in areas around the side opening must be designed to help compensate for the expansion characteristics of the side opening. Therefore, strut members adjacent to a side opening may be designed differently than strut members of the main body portion of the stent, and may experience higher stress levels, greater amounts of strain and provide less scaffolding support.

There remains a need for a stent having a side branch which exhibits superior expansion characteristics. It would further be desirable to provide a stent wherein strut design adjacent to a side opening provides a high level of scaffolding support and more closely matches the design of other portions of the stent.

The art referred to and/or described above is not intended to constitute an admission that any patent, publication or other information referred to herein is "prior art" with respect to this invention. In addition, this section should not be construed to mean that a search has been made or that no other pertinent information as defined in 37 C.F.R. §1.56(a) exists.

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

In at least one embodiment, a stent may have a longitudinal axis and may comprise a side branch cell. The side branch cell may comprise a plurality of petals including a first petal, and each petal may comprise a plurality of substantially straight struts and at least one turn. Each petal may have a central axis, and the central axis of the first petal may extend in a direction nonparallel to the stent longitudinal axis. At least two of said substantially straight struts of the first petal may extend substantially parallel to said stent longitudinal axis.

In another embodiment, a stent may comprise a body having a longitudinal axis and may be expandable from an unexpanded state to an expanded state. The stent body may define a plurality of interconnected strut members. A plurality of said interconnected strut members may comprise a plurality of petals, and the plurality of petals may define a side branch opening. Each petal may have a longitudinal axis and may further comprise at least one appendage. Each appendage may have a longitudinal axis and may comprise a first strut member, a turn and a second strut member. When the stent is in the unexpanded state, the longitudinal axis of each appendage may be substantially parallel to the longitudinal axis of the body.

These and other embodiments which characterize the invention are pointed out with particularity in the claims annexed hereto and forming a part hereof. However, for a better understanding of the invention, its advantages and objectives obtained by its use, reference should be made to the drawings which form a further part hereof and the accompanying descriptive matter, in which there are illustrated and described various embodiments of the invention.

BRIEF DESCRIPTION OF THE DRAWINGS

A detailed description of the invention is hereafter described with specific reference being made to the drawings.

DETAILED DESCRIPTION OF THE INVENTION

Figure 1:
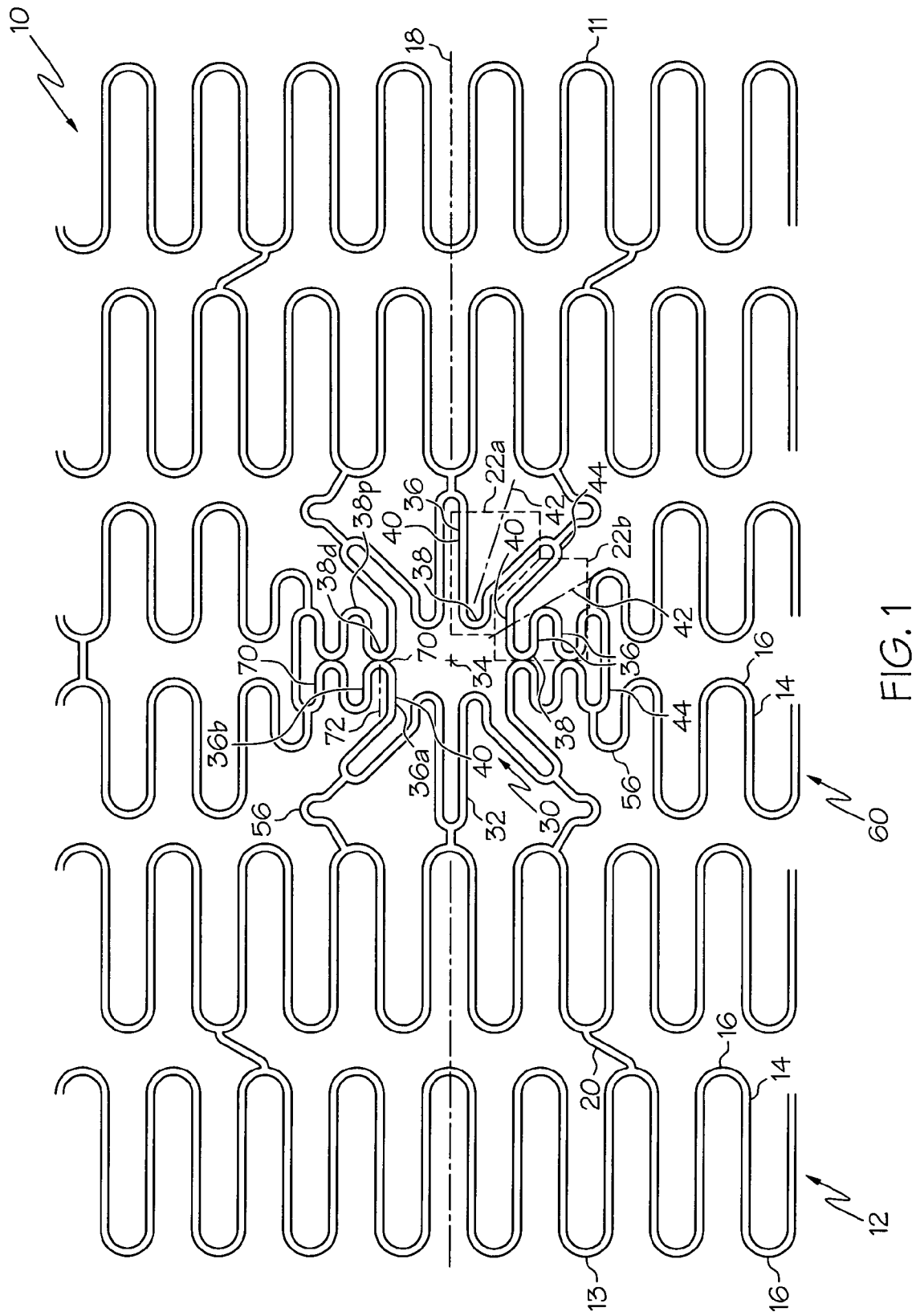
FIG. 1 shows an embodiment of a stent having a side branch cell.

While this invention may be embodied in many different forms, there are described in detail herein specific preferred embodiments of the invention. This description is an exemplification of the principles of the invention and is not intended to limit the invention to the particular embodiments illustrated.

For the purposes of this disclosure, like reference numerals in the figures shall refer to like features unless otherwise indicated. Use of the term "parallel" is intended to describe an orientation in which two elements may be exactly parallel or substantially parallel to one another.

The stent patterns depicted herein are generally shown and described as flat patterns. A person of ordinary skill in the art will understand that a cylindrical stent may be manufactured according to the design of the flat patterns disclosed.

Some examples of stents having a side opening and methods of deploying such stents are disclosed in U.S. Pat. Nos. 5,596,020 and 6,835,203, the entire disclosures of which are hereby incorporated herein in their entireties.

The entire disclosures of U.S. Pat. Nos. 5,922,021, 6,123,721, 6,334,870, 6,478,816, 6,348,065 and 6,325,826 are hereby incorporated herein by reference in their entireties.

FIG. 1 shows a flat pattern for an embodiment of a stent 10 which may include a side branch cell 30. The stent 10 may comprise a proximal end 11 and a distal end 13. The stent 10 may further comprise a plurality of serpentine bands 12 which may have any suitable shape, and in some embodiments may comprise a plurality of struts 14 connected by turns 16. Adjacent serpentine bands 12 may be connected by connectors 20.

A side branch cell 30 may comprise a continuous strut member 32, or in some embodiments a plurality of strut members, which may extend in serpentine fashion about the center 34 of the side branch cell 30. The side branch cell 30 desirably defines a plurality of side branch petals 40 which may have any suitable shape and may each be oriented in any suitable direction. A side branch cell 30 may have any suitable number of petals 40 and in some embodiments may have anywhere from six to ten petals 40. In some embodiments, the pattern of the continuous strut member(s) 32 may define the plurality of side branch petals 40.

FIG. 1 includes a reference box 22a drawn about a portion of the side branch cell 30 which may be defined as a petal 40. Reference box 22b indicates another portion of the side branch cell 30 which may be defined as a petal 40.

Each petal 40 may have an approximate longitudinal axis 42. In some embodiments, a petal 40 may have a longitudinal axis 42 which is oriented to extend substantially radially outwardly from the center 34 of the side branch cell 30. A longitudinal axis 42 may pass through the centroid of the stent elements which comprise the petal 40.

Each petal 40 may comprise a plurality of struts 36 and at least one turn 38. A strut 36 may be straight along its length, and may be oriented in any suitable direction. A turn 38 may be oriented in any suitable direction. In some embodiments, a turn 38 may comprise a proximal turn 38p oriented with a peak facing the proximal end 11 of the stent 10, or a distal turn 38d oriented with a peak facing the distal end 13 of the stent 10. Petals 40 which are adjacent to one another about the side branch cell 30 may be connected to one another by a connecting portion 44. In various locations, a connecting portion 44 may comprise a turn 38, a strut 36, or any combination of one or more turns 38 and one or more struts 36.

A petal 40 may include struts 36 that are oriented substantially parallel to the longitudinal axis 18 of the stent 10, and/or may include struts 36 that are oriented substantially parallel to the longitudinal axis 42 of the petal 40. In some embodiments, one or more struts 36 may be oriented at a range from 30° to 60° with respect to the longitudinal axis 18 of the stent 10. In some embodiments, one or more struts 36 may be oriented at approximately 45° with respect to the longitudinal axis 18 of the stent 10. In some embodiments, a petal may include a plurality of struts 36 that are oriented substantially parallel to the longitudinal axis 18 of the stent 10. This may be true even though the longitudinal axis 42 of the petal 40 may be oriented at an angle with respect to the longitudinal axis 18 of the stent 10. In some embodiments, a majority of the struts 36 or all of the struts 36 in a petal 40 may be oriented substantially parallel to the longitudinal axis 18 of the stent 10.

Each petal 40 may further comprise one or more appendages 70. An appendage 70 may comprise a first strut 36a and a second strut 36b connected by a turn 38. In some embodiments, an appendage 70 may include a proximal turn 38p, or may include a distal turn 38d. An appendage 70 may have an approximate longitudinal axis 72, and the approximate longitudinal axis 72 may be substantially parallel to the longitudinal axis 18 of the stent 10.

Figure 2:
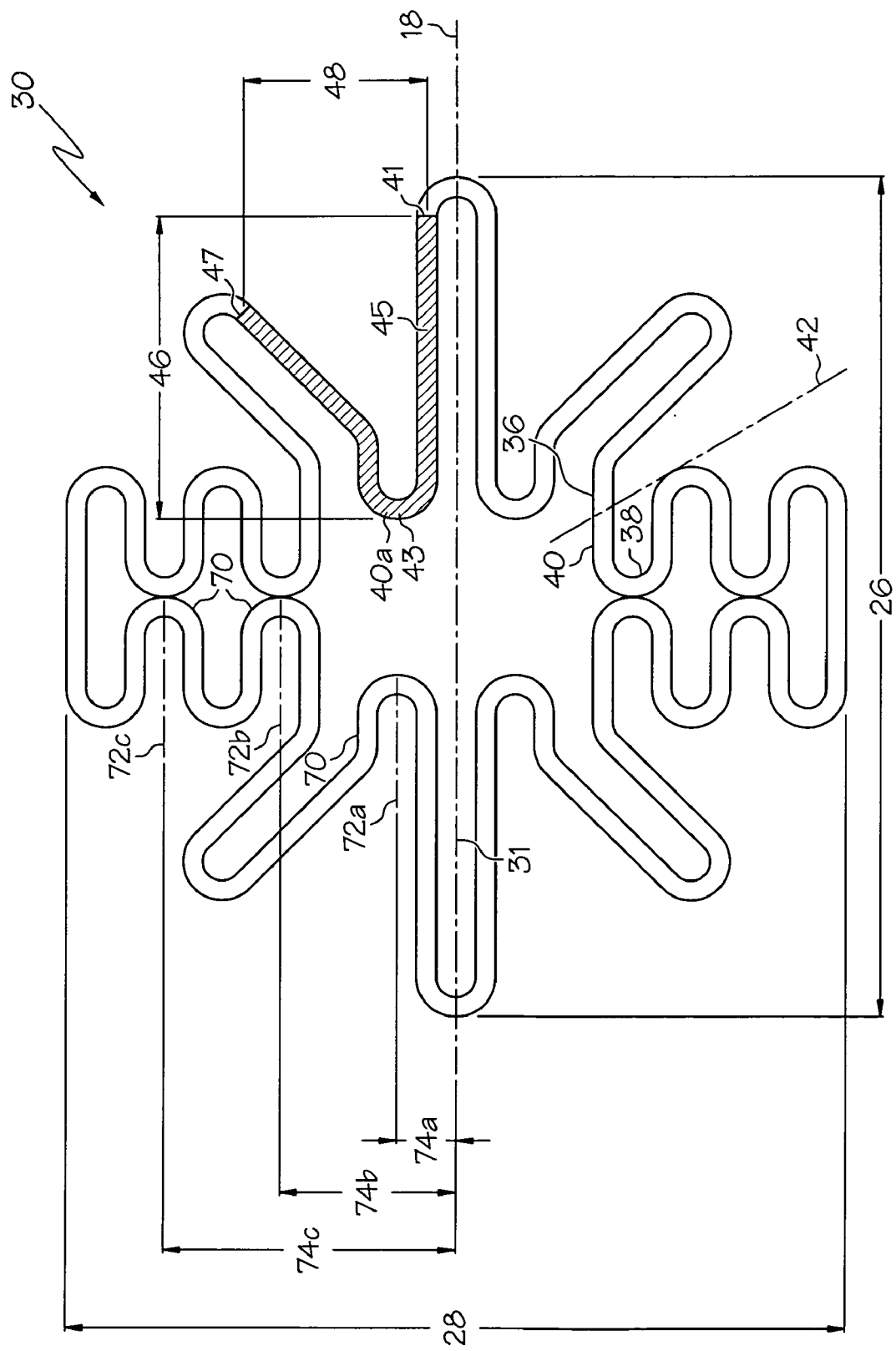
FIG. 2 shows an embodiment of a side branch cell.

FIG. 2 shows an embodiment of a side branch cell 30. Each petal 40 may occupy an area of space on the surface of the stent. For the purposes of the following disclosure, an embodiment of a petal 40a is shown with the approximate bounds of the petal 40a shaded. Each petal 40 may include a longitudinal length component 46 or a distance between a proximal most point (e.g. 41) and a distal most point (e.g. 43) of the petal 40 as measured in a direction parallel to the stent longitudinal axis 18. A proximal most point 41 may be defined as the point of a petal 40 that is closest to the proximal end 11 (see FIG. 1) of the stent, and a distal most point 43 may be defined as the point of a petal 40 that is closest to the distal end 13 (see FIG. 1) of the stent. Although a proximal most point 41 and a distal most point 43 are specifically indicated in FIG. 2 with respect to petal 40a, the location of a proximal most point and the location of a distal most point on any petal 40 may change as the shape of any petal 40 may change with stent crimping and/or stent expansion.

Each petal 40 may further include a circumferential length component 48, or a distance between opposed circumferential extremities 45, 47 of a petal 40 as measured in a direction about the circumference of the stent. As with the proximal most and distal most points 41, 43 of a petal 40, the locations of points which comprise the opposed circumferential extremities 45, 47 for a given petal 40 may change with stent crimping and/or stent expansion. The circumferential length component 48 of a petal 40 may be perpendicular to the longitudinal length component 46 of the petal 40.

Similar to the circumferential length component 48 and longitudinal length component 46 of a petal 40, a side branch cell 30 may include a longitudinal length component 26, or a distance between proximal most and distal most points of the side branch cell 30 as measured parallel to the stent longitudinal axis 18. A side branch cell 30 may also include a circumferential length component 28, or a distance between opposed extremities of the side branch cell 30 as measured in a direction about the circumference of the stent. The locations of a proximal most point, a distal most point, and the opposed circumferential extremities may change as a side branch cell 30 may change in size and shape with stent crimping and/or stent expansion. The longitudinal length component 26 of the side branch cell 30 may be perpendicular to the circumferential length component 28.

The geometric design of various embodiments of a side branch cell 30, including the design of the individual petals 40 within a side branch cell 30, desirably allows a stent 10 to expand more similarly to a standard stent not having a side branch cell 30. Desirably, upon expansion, the circumferential length component 28, 48 of a petal 40 or a side branch cell 30 may experience an increase that is proportionally larger than any related increase in the longitudinal length component 26, 46 of the respective petal 40 or side branch cell 30. In some embodiments, a longitudinal length component 26, 46 may remain the same or even reduce as the stent 10 expands. The geometric design of the petals 40, and particularly the petals 40 which have an approximate longitudinal axis 42 that is nonparallel to the stent longitudinal axis 18 and a plurality of struts 36 which are oriented substantially parallel to the stent longitudinal axis 18, allows for a relatively large increase in the circumferential length component 28, 48 as compared to any change (i.e. increase or decrease) in the longitudinal length component 26, 46 of the petal 40 or side branch cell 30 during stent expansion.

As a stent expands, the petals 40 may change shape, and the orientation of struts 36 and turns 38 may also change. Struts 36 which are substantially parallel to the stent longitudinal axis 18 in an unexpanded state may reorient on expansion and be nonparallel to the stent longitudinal axis 18 when the stent is expanded.

Appendages 70 may also change shape as the stent expands. In some embodiments, although an appendage 70 may change shape, the approximate longitudinal axis 72 of the appendage 70 may remain substantially parallel to the stent longitudinal axis 18 after expansion.

An appendage 70 may have a longitudinal axis 72 which is a predetermined distance away from a longitudinal axis 31 of the side branch cell 30, as measured in a stent circumferential direction. FIG. 2 shows a first longitudinal axis 72a, a second longitudinal axis 72b and a third longitudinal axis 72c for three respective appendages 70. Three respective predetermined distances 74a, 74b, 74c are shown between the side branch cell longitudinal axis 31 and the respective appendage longitudinal axes 72a, 72b, 72c.

As the stent expands, each appendage longitudinal axis 72 may displace away from the side branch cell longitudinal axis 31. The greater the distance 74 between the appendage longitudinal axis 72 and the side branch cell longitudinal axis 31, the greater the increase in the distance 74 may be. For example, during expansion, appendage longitudinal axis 72a may displace away from the side branch cell longitudinal axis 31. Appendage longitudinal axis 72b may also displace away from the side branch cell longitudinal axis 31. The amount of displacement of appendage longitudinal axis 72b may be greater than the amount of displacement of appendage longitudinal axis 72a. Similarly, appendage longitudinal axis 72c may also displace away from the side branch cell longitudinal axis 31, and the amount of displacement of appendage longitudinal axis 72c may be greater than the amount of displacement of appendage longitudinal axis 72b.

Referring again to FIG. 1, the stent 10 may include serpentine bands 12 which extend about an entire circumference of the stent 10. In some embodiments, serpentine bands 12 may be located in portions of stent length that do not include a side branch cell 30. In portions of length that do include a side branch cell 30, the stent 10 may include one or more partial serpentine bands 60, which may extend from one side of a side branch cell 30 about the circumference of the stent 10 to the other side of the side branch cell 30. The design of struts 14 and turns 16 in a partial serpentine band 60 may be similar to or different than the design geometry of the standard serpentine bands 12.

A stent 10 may include side branch connectors 56 which may connect between the side branch cell 30 and other portions of the stent 10. A side branch connector 56 may extend from any portion of a side branch cell 30, such as a petal 40 or connecting portion 44, and connect to any other portion of the stent 10, such as a serpentine band 12 or a partial serpentine band 60.

In some embodiments, a side branch connector 56 may include straight portions, peaks, valleys or other undulations. In some embodiments, a side branch connector 56 may comprise a flexible connector which may support an ostium when deployed in a vessel.

Desirably, the design of a side branch cell 30, and particularly the design of petals 40 having a plurality of struts 36 oriented substantially parallel to the stent longitudinal axis 10, may allow for more struts 14 and turns 16 in a partial serpentine band 60 than prior art designs. The design of a side branch cell 30 may also allow the design of the partial serpentine band(s) 60 to be consistent with the design of the standard serpentine bands 12. This allows the stent to provide more scaffolding support to vessel locations adjacent to the petal 40 region, particularly around juncture points between a main branch vessel and a side branch vessel, such as the carina and vessel areas contralateral to the carina.

The design of a side branch cell 30 also allows for the circumferential length component 28 of the side branch cell 30 to be further reduced as the stent 10 is further crimped to an unexpanded configuration which is more reduced than shown in FIG. 1. Minimizing the circumferential length component 28 in an unexpanded state may allow for additional stent elements, such as struts 14, in areas of the stent 10 adjacent to the side branch cell 30 about the circumference of the stent 10, for example in the partial serpentine band(s) 60.

Figure 3:
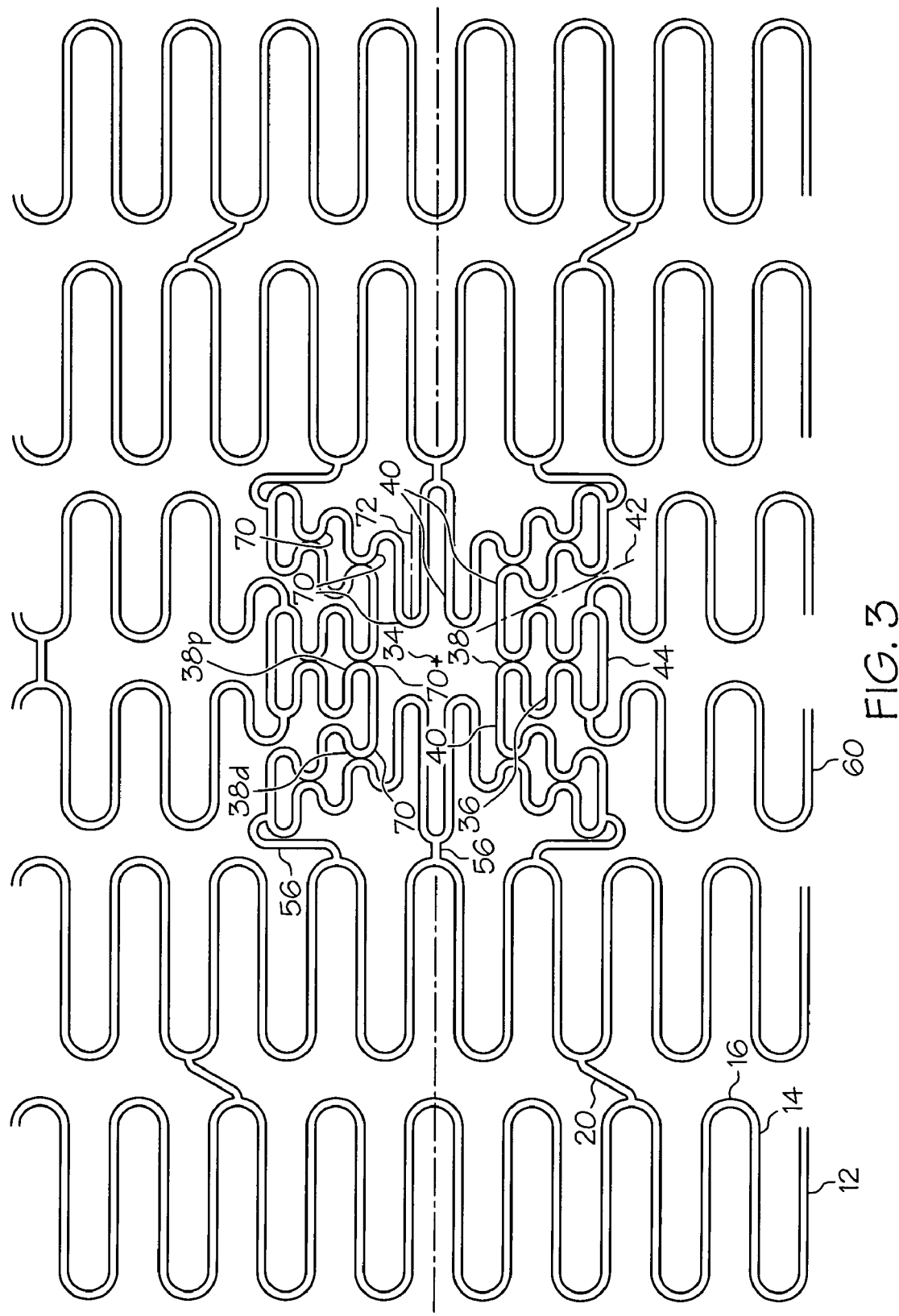
FIG. 3 shows another embodiment of a stent having a side branch cell.

FIG. 3 shows another embodiment of a side branch cell 30, which may comprise a continuous strut 32 which extends with serpentine undulations about a center 34 of the side branch cell 30. The side branch cell 30 may comprise a plurality of petals 40 which may be oriented in any suitable direction. In some embodiments, a petal 40 may have a longitudinal axis 42 which is oriented to extend substantially radially outwardly from the center 34 of the side branch cell 30. Each petal 40 may include a plurality of struts 36 and at least one turn 38. A strut 36 may be straight along its length. Petals 40 which are adjacent to one another about the side branch cell 30 may be connected to one another by a connecting portion 44.

All of the descriptions of a stent 10 and side branch cell 30 with respect to FIGS. 1 and 2 may be applied to FIG. 3. For example, each petal 40 may include a plurality of struts 36 that are oriented substantially parallel to the longitudinal axis 18 of the stent 10.

Each petal 40 may further comprise a plurality of appendages 70. A single petal 40 may include appendages 70 that are oriented in different or opposite directions. A single petal 40 may include at least one appendage having a proximal turn 38*p*, and at least one other appendage 70 having a distal turn 38*d*.

Figure 4:
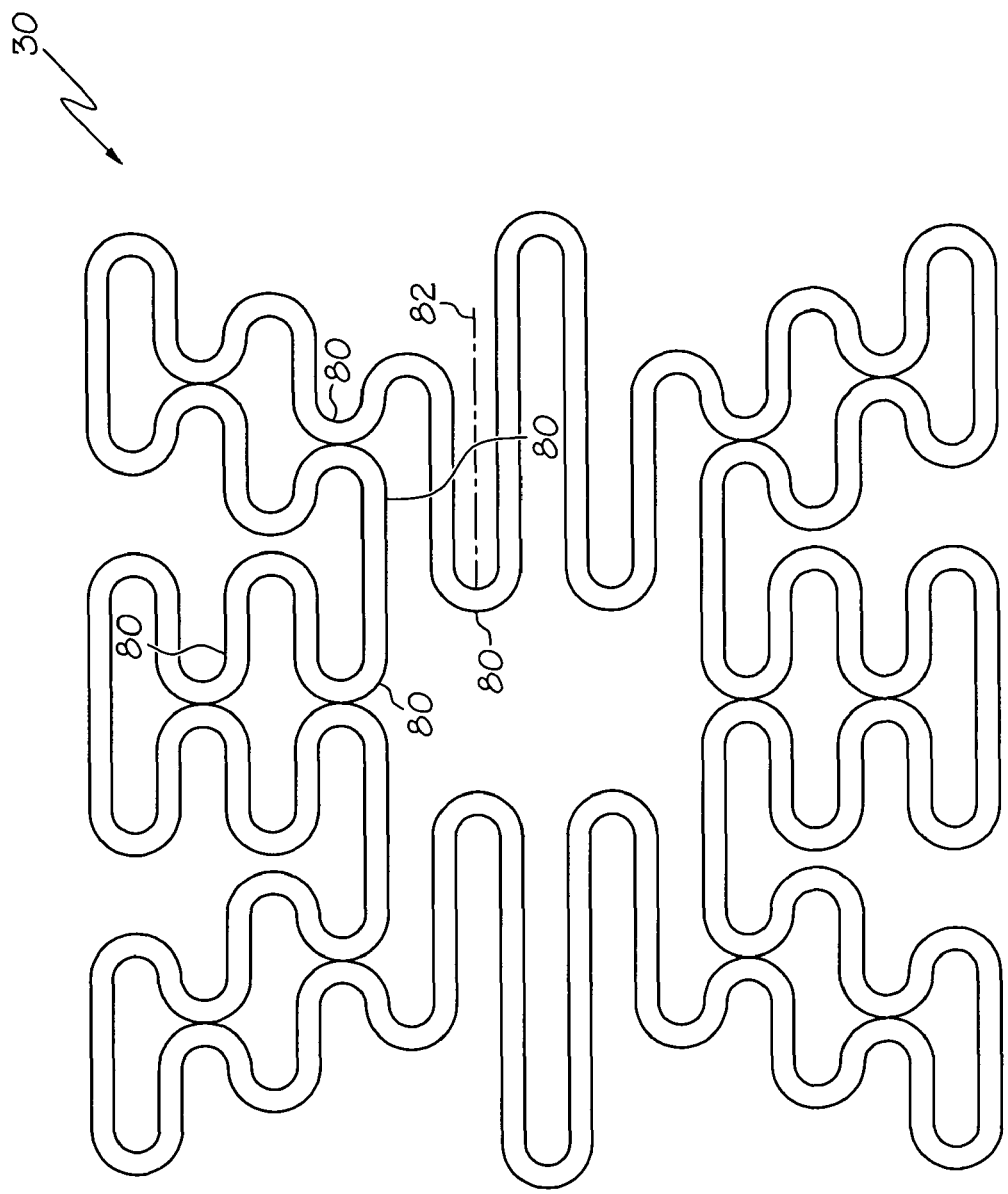
FIG. 4 shows an embodiment of a side branch cell.

FIG. 4 shows an embodiment of a side branch cell 30 which may have a plurality of petals 80. A side branch cell 30 may include a plurality of expansion states, such as a nominal state, a crimped or reduced state, and an expanded state. For example, a stent may be manufactured in the nominal state, and then be reduced in size to the crimped state. Upon stent expansion, the stent may assume the expanded state, which may be larger in size than the nominal state.

Each petal 80 may have a longitudinal axis 82. In at least a nominal state, petals 80 which are adjacent to one another along the length of the stent may have longitudinal axes 82 which share a common line. Petals 80 which are adjacent to one another about the circumference of the stent may have longitudinal axes 82 which are substantially parallel to one another. Petals 80 may have a longitudinal axis 82 which is substantially parallel to the longitudinal axis of the stent.

The inventive stents may be made from any suitable biocompatible materials including one or more polymers, one or more metals or combinations of polymer(s) and metal(s). Examples of suitable materials include biodegradable materials that are also biocompatible. By biodegradable is meant that a material will undergo breakdown or decomposition into harmless compounds as part of a normal biological process. Suitable biodegradable materials include polylactic acid, polyglycolic acid (PGA), collagen or other connective proteins or natural materials, polycaprolactone, hylauric acid, adhesive proteins, co-polymers of these materials as well as composites and combinations thereof and combinations of other biodegradable polymers. Other polymers that may be used include polyester and polycarbonate copolymers. Examples of suitable metals include, but are not limited to, stainless steel, titanium, tantalum, platinum, tungsten, gold and alloys of any of the above-mentioned metals. Examples of suitable alloys include platinum-iridium alloys, cobalt-chromium alloys including Elgiloy and Phynox, MP35N alloy and nickel-titanium alloys, for example, Nitinol.

The inventive stents may be made of shape memory materials such as superelastic Nitinol or spring steel, or may be made of materials which are plastically deformable. In the case of shape memory materials, the stent may be provided with a memorized shape and then deformed to a reduced diameter shape. The stent may restore itself to its memorized shape upon being heated to a transition temperature and having any restraints removed therefrom.

The inventive stents may be created by methods including cutting or etching a design from a tubular stock, from a flat sheet which is cut or etched and which is subsequently rolled or from one or more interwoven wires or braids. Any other suitable technique which is known in the art or which is subsequently developed may also be used to manufacture the inventive stents disclosed herein.

In some embodiments the stent, the delivery system or other portion of the assembly may include one or more areas, bands, coatings, members, etc. that is (are) detectable by imaging modalities such as X-Ray, MRI, ultrasound, etc. In some embodiments at least a portion of the stent and/or adjacent assembly is at least partially radiopaque.

In some embodiments, at least a portion of the stent is configured to include one or more mechanisms for the delivery of a therapeutic agent. Often the agent will be in the form of a coating or other layer (or layers) of material placed on a surface region of the stent, which is adapted to be released at the site of stent implantation or areas adjacent thereto.

A therapeutic agent may be a drug or other pharmaceutical product such as non-genetic agents, genetic agents, cellular material, etc. Some examples of suitable non-genetic therapeutic agents include but are not limited to: anti-thrombogenic agents such as heparin, heparin derivatives, vascular cell growth promoters, growth factor inhibitors, Paclitaxel, etc. Where an agent includes a genetic therapeutic agent, such a genetic agent may include but is not limited to: DNA, RNA and their respective derivatives and/or components; hedgehog proteins, etc. Where a therapeutic agent includes cellular material, the cellular material may include but is not limited to: cells of human origin and/or non-human origin as well as their respective components and/or derivatives thereof. Where the therapeutic agent includes a polymer agent, the polymer agent may be a polystyrene-polyisobutylene-polystyrene triblock copolymer (SIBS), polyethylene oxide, silicone rubber and/or any other suitable substrate.

The above disclosure is intended to be illustrative and not exhaustive. This description will suggest many variations and alternatives to one of ordinary skill in this field of art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the preferred and alternate embodiments of the invention. Those skilled in the art may recognize other equivalents to the specific embodiment described herein which equivalents are intended to be encompassed by the claims attached hereto.

The invention claimed is:

1. A stent having a longitudinal axis and comprising a side branch cell, the side branch cell defined by a plurality of petals including a first petal, each petal comprising a plurality of straight struts and at least two turns, each petal having a central axis, the central axis of the first petal extending in a direction nonparallel to the stent longitudinal axis, wherein at least two of said straight struts of the first petal extend parallel to said stent longitudinal axis when the stent is unexpanded.

2. The stent of claim 1, wherein the first petal further comprises a third straight strut oriented parallel to said stent longitudinal axis.

3. The stent of claim 2, wherein the first petal further comprises a fourth straight strut oriented parallel to said stent longitudinal axis.

4. The stent of claim 1, wherein said first petal further comprises a straight strut that is oriented an angle to the stent longitudinal axis, wherein the angle ranges from 30° to 60°.

5. The stent of claim 1, further comprising a second petal, the central axis of the second petal extending in a direction nonparallel to the stent longitudinal axis, wherein at least two of said straight struts of the second petal extend parallel to said stent longitudinal axis.

6. The stent of claim 1, wherein each petal includes at least two straight struts that are oriented parallel to said stent longitudinal axis.

7. The stent of claim 6, wherein the side branch cell comprises 6, 7, 8, 9 or 10 petals.

8. The stent of claim 1, wherein the side branch cell includes a longitudinal length component and a circumferential length component, wherein as a diameter of the stent increases, an increase in the circumferential length component is greater than any change in the longitudinal length component.

9. The stent of claim 1, wherein said first petal includes a longitudinal length component component and a circumferential length component, wherein as a diameter of the stent increases, an increase in the circumferential length component is greater than any change in the longitudinal length component.

10. The stent of claim 1, wherein each petal includes a longitudinal length component and a circumferential length component, wherein as a diameter of the stent increases, for each petal an increase in the circumferential length component is greater than any change in the longitudinal length component.

11. The stent of claim 1, wherein the first petal further comprises a plurality of appendages, each appendage having a longitudinal axis oriented parallel to said stent longitudinal axis.

12. The stent of claim 11, wherein the longitudinal axis of each appendage remains parallel to said stent longitudinal axis as the stent is expanded.

13. A stent comprising a body having a longitudinal axis, the body defining a plurality of interconnected strut members, a plurality of said interconnected strut members comprising a plurality of petals, the plurality of petals forming a closed perimeter that defines a side branch opening, each petal comprising at least one appendage having a longitudinal axis that is parallel to the longitudinal axis of the body when the stent is unexpanded.

14. A stent comprising a body having a longitudinal axis, the stent being expandable from an unexpanded state to an expanded state, the body defining a plurality of interconnected strut members, a plurality of said interconnected strut members comprising a plurality of petals, the plurality of petals forming a closed perimeter that defines a side branch opening, each petal having a longitudinal axis, each petal further comprising at least one appendage, each appendage comprising a first strut member, a turn and a second strut member, each appendage having a longitudinal axis, wherein when the stent is in the unexpanded state, the longitudinal axis of each appendage is parallel to the longitudinal axis of the body.

15. The stent of claim 14, wherein a first petal comprises a first appendage and a second appendage.

16. The stent of claim 15, wherein the turn of said first appendage is oriented toward a proximal end of the stent, and wherein the turn of said second appendage is oriented toward the proximal end of the stent.

17. The stent of claim 15, wherein the turn of said first appendage is oriented toward a proximal end of the stent, and wherein the turn of said second appendage is oriented toward a distal end of the stent.

18. The stent of claim 14, wherein each petal further comprises a plurality of appendages.

19. The stent of claim 14, wherein the longitudinal axis of a first petal is nonparallel to the longitudinal axis of the body.

20. The stent of claim 14, wherein the longitudinal axis of an appendage remains parallel to the longitudinal axis of the body as the stent is expanded.

21. The stent of claim 1, wherein each straight strut comprises a length that is greater than its width.

22. The stent of claim 1, wherein said plurality of petals extend continuously around said side branch cell.

23. The stent of claim 1, wherein the side branch cell comprises a central branch opening.

* * * * *